United States Patent [19]

Arkans

[11] 4,338,944
[45] Jul. 13, 1982

[54] THERAPEUTIC DEVICE
[75] Inventor: Edward J. Arkans, Schaumburg, Ill.
[73] Assignee: The Kendall Company, Boston, Mass.
[21] Appl. No.: 159,708
[22] Filed: Jun. 16, 1980
[51] Int. Cl.³ .............................................. A61F 7/00
[52] U.S. Cl. .................................... 128/400; 128/402
[58] Field of Search ................ 128/400, 402, 403, 399

[56] References Cited

U.S. PATENT DOCUMENTS

| | | |
|---|---|---|
| 484,182 | 10/1892 | Dewey . |
| 3,074,410 | 1/1963 | Foster ................................. 128/400 |
| 3,088,288 | 5/1963 | Elfving ...................................... 62/3 |
| 3,186,404 | 6/1965 | Gardner ............................... 128/87 |
| 3,238,944 | 3/1966 | Hirschhorn ........................ 128/400 |
| 3,262,492 | 7/1966 | Meenan ................................ 165/27 |
| 3,548,819 | 12/1970 | Davis et al. ......................... 128/402 |
| 3,738,372 | 6/1973 | Shioshvili ............................ 128/400 |
| 3,865,116 | 2/1975 | Brooks ................................. 128/400 |
| 3,871,381 | 3/1975 | Roslonski ........................... 128/400 |
| 3,889,684 | 6/1975 | Lebold ................................. 128/402 |
| 3,901,225 | 8/1975 | Sconce ................................. 128/402 |
| 3,967,627 | 7/1976 | Brown ................................. 128/400 |
| 4,149,541 | 4/1979 | Gammons et al. ................. 128/400 |
| 4,259,961 | 4/1981 | Hood ................................... 128/402 |

FOREIGN PATENT DOCUMENTS

| | | |
|---|---|---|
| 1262837 | 4/1961 | France . |
| 392779 | 5/1933 | United Kingdom . |
| 1178916 | 1/1970 | United Kingdom . |
| 1386728 | 3/1975 | United Kingdom . |
| 1462003 | 1/1977 | United Kingdom . |
| 1467729 | 3/1977 | United Kingdom . |
| 1521752 | 8/1978 | United Kingdom . |
| 2002235 | 2/1979 | United Kingdom . |
| 2057268 | 8/1979 | United Kingdom . |
| 1566207 | 4/1980 | United Kingdom . |
| 2064330 | 6/1981 | United Kingdom . |

OTHER PUBLICATIONS

Cryomed Devices Inc., Advertisement for CRYO-PAC TM, Cold Compress Kit, (copyright 1974).
"Thermoelectric Coolers Tackle Jobs Heat Sinks Can't", Jim McDermott, Spec. Ed., for EDN, May 20, 1980, pp. 111-117.
United Surgical Supplies brochure.

Primary Examiner—Kyle L. Howell
Assistant Examiner—C. W. Shedd
Attorney, Agent, or Firm—Powell L. Sprunger

[57] ABSTRACT

A therapeutic device comprising, a sleeve for covering a portion of a patient's body and having a space to receive liquid, a device for circulating a liquid through the space of the sleeve, and a device for cooling the circulated liquid.

14 Claims, 9 Drawing Figures

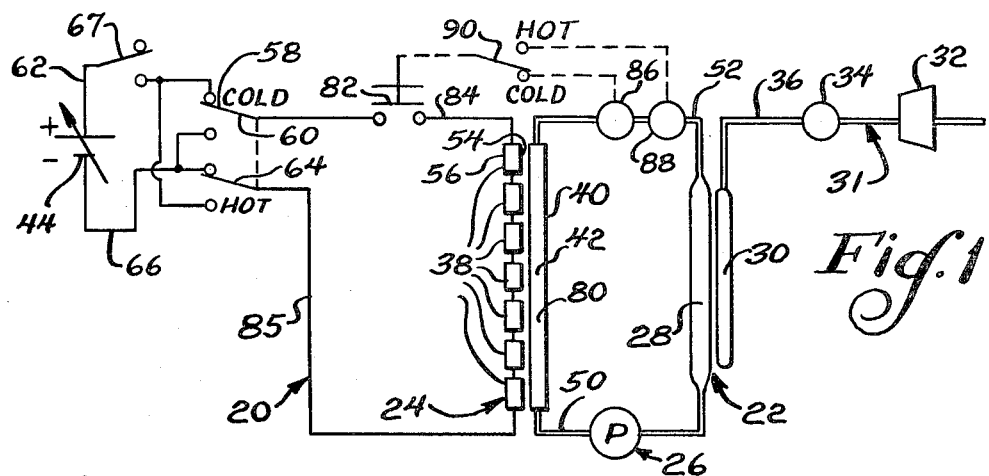
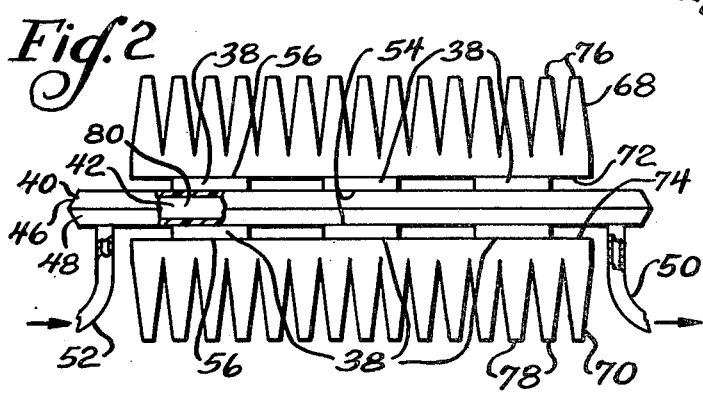
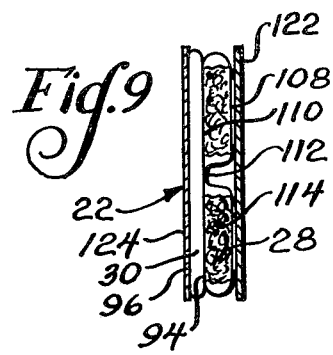
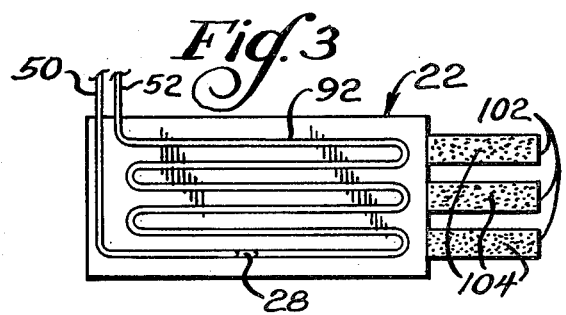
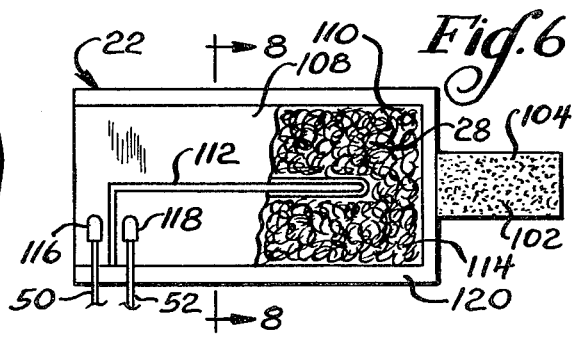
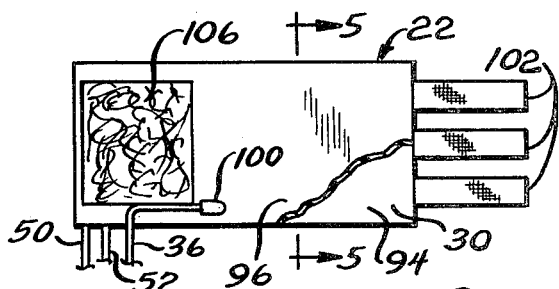
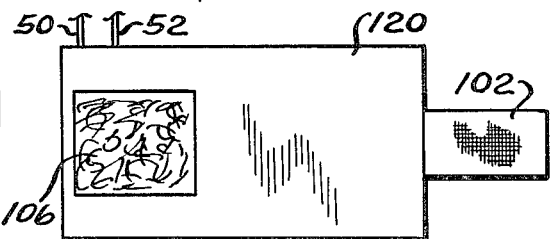
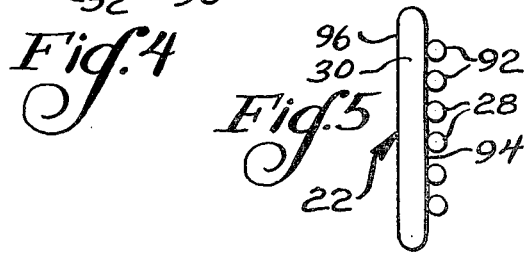
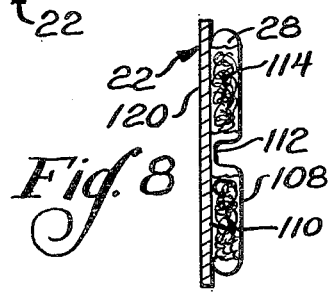

THERAPEUTIC DEVICE

BACKGROUND OF THE INVENTION

The present invention relates to therapeutic devices for patients.

Cryotherapy may be defined as the treatment of a patient with cold. In many instances it is desirable to cool and apply pressure to the tissue of the patient. For example, sports trainers often wish to apply cold and pressure to the extremities, hands, feet, or joints of an athlete after a sprain or strain sustained during playing. Similarly, physicians in hospitals, such as in emergency rooms, often desire to apply cold and pressure to a patient in order to accelerate healing by reducing edema and hematoma. It is also believed that the application of cold and pressure may be useful for spinal injuries. Not only does cold and pressure serve for the treatment of tissue injuries, it also acts as an anesthetic to reduce pain.

In the past, the necessary coldness has been most commonly obtained through the use of ice. It is apparent that such a procedure is cumbersome and inconvenient, and the desired coldness may not be obtained. In certain instances, it is desirable to apply cold and pressure for protracted periods of time which is not feasible without frequent changes of ice. In some instances, it is desirable to apply heat after cryotherapy has been completed which of course cannot be accomplished with ice.

SUMMARY OF THE INVENTION

A principal feature of the pesent invention is the provision of a therapeutic device for use in cryotherapy.

The device of the present invention comprises, a sleeve for covering a portion of a patient's body and having a space to receive liquid. The device has means for circulating a liquid through the space of the sleeve, and means for cooling the circulated liquid.

A feature of the present invention is that the sleeve may be placed against the patient's body to apply cold treatment to the patient.

Another feature of the invention is the provision for applying pressure by the sleeve against the patient during the cold treatment.

A further feature of the invention is the provision of means for inhibiting the cooling means and for heating the circulated liquid.

Thus, a feature of the invention is that the sleeve may be utilized to selectively apply cold or heat to the patient.

Another feature of the invention is that the temperature of the cooling and heating means may be controlled.

Yet another feature of the invention is the provision of specific sleeves which are designed for application of cold or heat to the patient.

Further features will become more fully apparent in the following description of the embodiments of this invention and from the appended claims.

DESCRIPTION OF THE DRAWINGS

In the drawings:

FIG. 1 is a schematic view of a therapeutic device of the present invention;

FIG. 2 is a fragmentary side elvational view, partly broken away, of a cooling and heating device for the device of FIG. 1;

FIG. 3 is a fragmentary front plan view of a sleeve for the device of FIG. 1;

FIG. 4 is a fragmentary back plan view, partly broken away, of the sleeve of FIG. 3;

FIG. 5 is a sectional view taken substantially as indicated along the line 5—5 of FIG. 4;

FIG. 6 is a fragmentary front plan view, partly broken away, of another embodiment of a sleeve for the device of FIG. 1;

FIG. 7 is a fragmentary back plan view of the sleeve of FIG. 6;

FIG. 8 is a sectional view taken substantially as indicated along the line 8—8 of FIG. 6; and FIG. 9 is a sectional view of another embodiment of a sleeve for the device of FIG. 1.

DESCRIPTION OF THE PREFERRED EMBODIMENTS

Referring now to FIG. 1, there is shown a therapeutic device generally designated 20 comprising a sleeve 22 for covering a portion of a patient's body, such as the extremities, a cooling and heating device 24, and a device such as a pump 26 for circulating liquid through the sleeve 22 and device 24. As will be further discussed below, the sleeve 22 has an inner space 28 to receive the circulating liquid, and may have an inflatable external chamber 30 to apply pressure in the sleeve 22 against the space 28 which is retained adjacent the patient's body. The device 20 may have an inflation device 31 comprising an air compressor 32 and a pressure regulator 34 in order to inflate the chamber 30 through a conduit 36.

The cooling and heating device 24 comprises a plurality of thermoelectric devices or thermoelectric cooling modules 38, a metallic container 40 having a chamber 42 to retain a liquid 80 such as water or antifreeze, and a variable direct current power supply 44. With reference to FIGS. 1 and 2, the container 40 comprises a pair of metallic shells 46 and 48 which have cavities such that the shells 46 and 48 define the chamber 42 when the shells 46 and 48 are placed together. In a suitable form, the shells 46 and 48 may be constructed from copper in order to facilitate heat transfer through the shells 46 and 48. The device 20 has an outlet conduit 50 communicating with the chamber 42 and one side of the sleeve space 28, with the pump 26 being connected to the conduit 50, as shown. The device 20 also has an inlet conduit 52 communicating between the chamber 42 and the other side of the sleeve space 28. During operation, the pump 26 circulates the cooling and heating liquid 80 through the conduit 50, the sleeve space 28, the conduit 52, and the container chamber 42, such that the described arrangement circulates the liquid 80 between the container 40, where the liquid is cooled or heated, and the sleeve 22 through use of the pump 26.

The thermoelectric devices 38 operate in the following manner. When direct current is passed in one direction through the thermoelectric devices 38, one side or face 54 of the thermoelectric devices 38 is cooled, while the other side or face 56 of the thermoelectric devices 38 is heated. When the direction of the direct current through the thermoelectric devices 38 is reversed, the one face 54 of the thermoelectric devices 38 is heated, while the other face 56 of the thermoelectric devices 38 is cooled. The device 20 has a double pole, double throw switch 58 in order to control the direction of current through the thermoelectric devices 38, with the switch 58 being connected to the thermoelectric devices 38, which are connected in series, by a pair of leads 84 and 85. When the switch 58 is connected to the "cold" setting, as shown, with the contact 60 and lead 84 being connected to the lead 62, and with the contact 64 and lead 85 being connected to the lead 66, the direction of the current from the power supply 44 through the thermoelectric devices 38 is such that the one face 54 of the devices 38 is cooled, while the other face 56 of the devices 38 is heated. When the switch 58 is moved to the "hot" setting, with the contact 60 and lead 84 being connected to the lead 66, and with the contact 64 and lead 85 being connected to the lead 62, the direction of the current from the power supply 44 through the thermoelectric devices 38 is reversed, such that the one face 54 of the thermoelectric devices 38 is heated, while the other face 56 of the thermoelectric devices 38 is cooled. The lead 62 may have an on/off switch 67 in order to control application of power to the thermoelectric devices 38.

With reference to FIG. 2, the thermoelectric devices 38 are placed on opposed sides of the container 40, with the one face 54 of the thermoelectric devices 38 facing toward and in contact with the walls of the container 40, and with the other face 56 of the thermoelectric devices 38 facing away from the container 40. In the illustrated configuration, three thermoelectric devices 38 are placed on one side of the container 40, and three thermoelectric devices 38 are placed on the other side of the container 40. As shown, the device 20 has a pair of heat sinks 68 and 70 having generally planar surfaces 72 and 74, respectively, and a plurality of fins 76 and 78, respectively. The surfaces 72 and 74 of the heat sinks 68 and 70 are in contact with the other face 56 of the thermoelectric devices 38. As previously discussed in connection with FIGS. 1 and 2, when the switch 58 is connected to the "cold" setting, the one face 54 of the thermoelectric devices 38 is cooled, and the other face 56 of the thermoelectric devices 38 is heated. In this switch configuration, the heat sinks 68 and 70 are utilized to dissipate heat from the other face 56 of the thermoelectric devices 38, while the one face 54 of the thermoelectric devices 38 cools the liquid 80 in the chamber 42 through the metallic shells 46 and 48.

Thus, when the switch 58 is placed in the "cold" setting, the liquid 80 is cooled in the container chamber 42, and the pump 26 circulates the cooled liquid 80 through the conduit 50 to the space 28 in the sleeve 22, with the pump 26 also recirculating the liquid 80 from the sleeve space 28 through the conduit 52 to the container chamber 42 for additional cooling. Of course, during use of the device 20, the sleeve space 28 is placed toward the patient in order to cool the patient's body by the cold liquid in the space 28. Alternatively, when the switch 58 is placed in the "hot" setting, the liquid 80 in the container chamber 42 is heated, and the pump 26 circulates the heated liquid 80 through the conduit 50 into the sleeve space 28, with the pump 26 also recirculating the liquid 80 from the space 28 through the conduit 52 to the container chamber 42 for additional heating. Thus, in this configuration of the switch 58, the sleeve space 28 may be utilized to apply heat to the patient's body. Accordingly, the device 20 may apply cold or heat to the patient for treatment in accordance with the setting of the switch 58.

As shown in FIG. 1, the device 20 has a switch or relay 82 operatively associated with the lead 84. The device 20 may have a pair of thermostats 86 and 88, such as temperature sensors, which measure the temperature of the liquid 80 in the circulating system. The device 20 may have a switch 90 to control the operative connection of the thermostats 86 and 88 to the switch or relay 82. When the switch 90 is placed in the "cold" setting, the thermostat 86 is operatively connected to the switch or relay 82 such that the switch 82 is closed or the relay 82 is placed in the closed setting when the thermostat 86 determines that the cooling liquid 80 is not sufficiently cold in order to provide current to the thermoelectric devices 38 and cause cooling; of course, the switch 58 is also placed in the "cold" setting at this time. On the other hand, the switch 82 is opened or the relay 82 is placed in the open setting when the thermostat 86 determines that the liquid 80 is at or below the desired temperature, in order to remove current from the thermoelectric devices 38 and stop cooling. Alternatively, when the switch 90 is placed in the "hot" setting, the switch 82 is closed or the relay 82 is placed in the closed setting when the thermostat 88 determines that the liquid is not sufficiently hot in order to provide current to the thermoelectric devices 38 and cause heating; of course, the switch 58 is also placed in the "hot" setting at this time. On the other hand, the switch 82 is opened or the relay 82 is placed in the open setting when the thermostat 88 determines that the temperature is at or above the desired temperature of the circulating liquid 80 in order to remove current from the thermoelectric devices 38 and stop heating. Thus, the temperature of the circulating liquid 80 may be controlled whether the liquid 80 is being cooled or heated. In an alternative form, the switch or relay 82 may be closed, and the voltage of the power supply 44 may be varied in order to change the current through the thermoelectric devices 38 and raise or lower the temperature, as desired.

A sleeve 22 for the device 20 of FIG. 1 is illustrated in FIGS. 3-5. The sleeve has an elongated conduit 92 connected between the inlet and outlet conduits 52 and 50. The conduit 92 is located on an inner or front portion of the sleeve 22, and the conduit 92 may be placed in a serpentine configuration, as shown, with a lumen in the conduit 92 defining the space 28 for the cooling or heating liquid 80. The sleeve 22 has a front wall 94 and a back wall 96 of flexible plastic material, with the walls 94 and 96 being joined at their periphery, such as by heat sealing, to define the chamber 30 between the walls 94 and 96. As shown, the walls 94 and 96 are located above the conduit 92 and preferably cover the conduit 92, with the conduit 92 being attached to the front wall 94. The sleeve 22 has a connector 100 attached to the back wall 96 and communicating with the chamber 30. As shown, the conduit 36 of the inflation device 31 is connected to the connector 100, such that the conduit 36 communicates with the chamber 30. Thus, the chamber 30 may be inflated by the inflation device 31 through the conduit 36 and connector 100.

As shown, the sleeve 22 has a plurality of straps 102 extending from one end of the sleeve 22 with hook fastening strips 104 being secured to a front face of the straps 102. The sleeve 22 also has a sheet 106 of loop fastening material secured to the outer surface of the back wall 96 on the other end of the sleeve 22 remote the straps 102.

In use, the conduit 92 of the sleeve 22 may be placed against an extremity of a patient, and the sleeve 22 may be wrapped around the extremity. Next, the hook fastening strips 104 of the straps 102 are secured to the sheet 106 of loop fastening material in order to secure the sleeve 22 in place on the extremity. Once the sleeve 22 has been secured to the patient, the chamber 30 may be inflated through the conduit 36 in order to apply pressure by the conduit 92 against the patient's extremity. The liquid 80 may then be circulated through the conduit 92 in order to cool or heat the patient's extremity as desired while applying pressure to the patient's extremity.

Another embodiment of the sleeve 22 for the device 20 is illustrated in FIGS. 6–8, in which like reference numerals designate like parts. In this embodiment, the sleeve 22 has a front wall 108 of flexible plastic material, and a back wall 110 of flexible plastic material. The front and back walls 108 and 110 are joined at their peripheries, such as by heat sealing, and along an intermediate line 112 to define the space 28 intermediate the front and back walls 108 and 110. The sleeve 22 has a sheet 114 of open cell foam which is cut to the size of the space 28 and which is placed in the space 28 between the front and back walls 108 and 110. The sleeve 22 has a pair of connectors 116 and 118 connected to the front wall 108 on opposed sides of the sealing line 112, with the connectors 116 and 118 communicating with the space 28 in the sleeve 22. As shown, the outlet conduit 50 is connected to the connector 116, and the inlet conduit 52 is connected to the connector 118, such that the conduits 50 and 52 communicate with the opposed ends of the serpentine space 28 in the sleeve 22.

The sleeve 22 has a rear sheet 120 of insulation material, such as closed cell foam, covering the back wall 110. The sleeve 22 has a strap 102 extending from one end of the sheet 120, with a strip 104 of hook fastening material being secured on the front face of the strap 102. The sleeve 22 also has a sheet 106 of loop fastening material secured to an outer face of the sheet 120 adjacent the other end of the sheet 120.

In use, the front wall 108 of the sleeve 22 is placed against the extremity of a patient, and the sleeve is wrapped around the extremity. Next, the hook fastening strip 104 on the strap 102 is secured to the sheet 106 of loop fastening material in order to secure the sleeve 22 in place on the extremity and apply pressure by the sheet 120 against the walls 108 and 110 defining the space 28. Next, the cold or hot liquid 80 is circulated through the conduits 50 and 52 and through the space 28 between the walls 108 and 110 in order to apply cold or heat to the patient's extremity through the front wall 108 while the sheet 120 applies pressure by the sleeve 22 against the patient's extremity. When secured to the patient, the sheet 120 serves to insulate the circulating cold or hot liquid 80 in order to limit passage of heat to or from the liquid 80 in the space 28. Also, the resilient sheet 114 of open cell foam material permits passage of liquid, but maintains the walls 108 and 110 in a spaced apart configuration at a plurality of locations, such that the applied pressure does not impede flow of liquid through the space 28. In addition, the sheet 114 of open cell foam causes circulation and mixture of the liquid in the space 28 in order to provide a more uniform distribution of temperature in the space 28.

Another embodiment of the sleeve 22 for the device 20 is illustrated in FIG. 9, in which like reference numerals designate like parts. In this embodiment, the sleeve 22 has a front and back wall 108 and 110 which are joined together to define space 28 and which receive a sheet 114 of open cell foam intermediate the walls 108 and 110 in a manner as previously described in connection with the sleeve 22 of FIGS. 6–8. Also, the sleeve 22 may have a front wall 94 and a back wall 96 of flexible plastic material joined together at their peripheries in order to define an inflatable chamber 30 intermediate the walls 94 and 96 in a manner similar to the sleeve 22 previously described in connection with FIGS. 3–5. The sleeve 22 may have a front sheet 122 of flexible conformable material, such as a nonwoven material, with the sheet 122 covering the front wall 108. In addition, the sleeve 22 may have a back sheet 124 of flexible inelastic material, such as a suitable textile material.

In use, the sleeve 22 of FIG. 9 is wrapped around the patient's extremity and may be secured in place using hook and loop fastening strips in a manner as previously described in connection with the sleeves of FIGS. 3–8. Next, the chamber 30 may be inflated by the inflation device 31 in a manner as previously described in order to apply pressure by the sleeve 22 against the patient's extremity, with the outer sheet 124 limiting expansion of the chamber 30 to enhance the pressures applied by the sleeve 22. The hot or cold liquid 80 may then be passed into the space 28 in order to apply heat or cold through the sheet 122 to the patient's extremity, while the sheet 114 of open cell foam maintains the space 28 in an open configuration. During use of the sleeve 22, the sheet 122 provides a comfortable surface of the sleeve 22 for contacting the patient's skin.

The foregoing detailed description is given for clearness of understanding only, and no unnecessary limitations should be understood therefrom, as modifications will be obvious to those skilled in the art.

I claim:

1. A therapeutic device, comprising:
a sleeve for covering a portion of a patient's body and having a pair of opposed flexible liquid impervious walls defining a space to receive liquid, said sleeve having a sheet of substantially nonabsorbent open cell foam in the space between said walls;
means for circulating a liquid through said space of the sleeve; and
means for selectively heating and cooling the circulated liquid at a location remote from the sleeve comprising a container having opposed metallic walls defining a chamber, a plurality of thermoelectric devices arranged on the outer surfaces of both walls, each thermoelectric device having one side in contact with a chamber wall, heat sink means on each side of the container, each thermoelectric device having a side opposite said one side in contact with said heat sink, a D.C. power supply, and control means for selectively directing current through said thermoelectric devices in one direction, whereby liquid in said chamber is caused to be heated, and in a direction opposite said one direction, whereby liquid in said chamber is caused to be cooled.

2. A therapeutic device, comprising:
a sleeve having an elongated conduit arranged in a serpentine configuration and defining a space to receive liquid;
means for circulating a liquid through the space of the sleeve; and
means for selectively heating and cooling the circulated liquid at a location remote from the sleeve comprising a container having opposed metallic walls defining a chamber, a plurality of thermoelectric devices arranged on the outer surfaces of both walls, each thermoelectric device having one side in contact with a chamber wall, heat sink means on each side of the container, each thermoelectric device having a side opposite said one side in contact with said heat sink, a D.C. power supply, and control means for selectively directing current through said thermoelectric devices in one direction, whereby liquid in said chamber is caused to be heated, and in a direction opposite said one direction, whereby liquid in said chamber is caused to be cooled.

3. The device of claim 1 or 2 including means for applying pressure to the portion of said sleeve containing said space.

4. The device of claim 3 wherein the pressure applying means comprises a pair of flexible walls in the sleeve outside said space defining a chamber, and means for inflating said chamber.

5. The device of claim 4 including a sheet of flexible material outside the walls in the sleeve defining said chamber.

6. The device of claim 3 wherein the pressure applying means comprises a sheet of flexible material in the sleeve outside said space.

7. The device of claim 6 wherein said sheet comprises an insulation material.

8. The device of claim 7 wherein said sheet comprises a closed cell foam material.

9. The device of claim 3 wherein the pressure applying means is located in said sleeve, and including means for securing the sleeve about an extremity of the patient.

10. The device of claim 1 or 2 including a sheet of flexible material in the sleeve at an inner location relative said space.

11. The device of claim 1 or 2 including means for applying pressure to the walls of the sleeve.

12. The device of claim 1 or 2 wherein the circulating means comprises a pump.

13. The device of claim 12 wherein the circulating means includes conduit means connecting the pump to the sleeve space.

14. The device of claim 1 or 2 including means for controlling the temperature of the heating and cooling means.

* * * * *